(12) United States Patent
Griffin

(10) Patent No.: US 8,328,791 B2
(45) Date of Patent: Dec. 11, 2012

(54) SELECTIVELY FLEXIBLE CATHETER AND METHOD OF USE

(75) Inventor: Stephen Griffin, San Jose, CA (US)

(73) Assignees: Stryker Corporation, Kalamazoo; Stryker NV Operations Limited, Dublin (IE)

( * ) Notice: Subject to any disclaimer, the term of this patent is extended or adjusted under 35 U.S.C. 154(b) by 181 days.

(21) Appl. No.: 12/939,895

(22) Filed: Nov. 4, 2010

(65) Prior Publication Data

US 2011/0054393 A1 Mar. 3, 2011

Related U.S. Application Data

(63) Continuation of application No. 11/004,544, filed on Dec. 3, 2004, now Pat. No. 7,828,790.

(51) Int. Cl.
*A61M 25/00* (2006.01)

(52) U.S. Cl. ........................ 604/525; 604/530

(58) Field of Classification Search .... 604/95.01–95.05, 604/113, 523–532
See application file for complete search history.

(56) References Cited

U.S. PATENT DOCUMENTS

| | | | |
|---|---|---|---|
| 3,416,531 A | 12/1968 | Edwards | |
| 3,485,234 A | 12/1969 | Stevens | |
| 3,612,038 A | 10/1971 | Halligan | |
| 3,612,058 A | 10/1971 | Ackerman | |
| 3,725,116 A | 4/1973 | Parker et al. | |
| 4,210,478 A | 7/1980 | Shoney | |
| 4,292,270 A | 9/1981 | Hannah et al. | |
| 4,341,218 A | 7/1982 | Ü | |
| 4,359,453 A | 11/1982 | Gordon | |
| 4,369,206 A | 1/1983 | Mayer et al. | |
| 4,385,635 A | 5/1983 | Ruiz | |
| 4,419,095 A | 12/1983 | Nebergall et al. | |
| 4,427,000 A | 1/1984 | Ueda | |
| 4,516,970 A | 5/1985 | Kaufman et al. | |
| 4,516,972 A | 5/1985 | Samson | |
| 4,531,943 A | 7/1985 | Van Tassel et al. | |
| 4,563,181 A | 1/1986 | Wijayarathna et al. | |
| 4,588,399 A | 5/1986 | Nebergall et al. | |
| 4,590,922 A | 5/1986 | Gordon | |
| 4,622,953 A | 11/1986 | Gordon | |

(Continued)

FOREIGN PATENT DOCUMENTS

EP 0180348 5/1986

(Continued)

OTHER PUBLICATIONS

Kolobow et al., "A New Thin-Walled Nonkinking Catheter for Peripheral Vascular Cannulation," *Surgery*, vol. 68, No. 4, Oct. 1970, pp. 625-626.

(Continued)

*Primary Examiner* — Nicholas Lucchesi
*Assistant Examiner* — Gerald Landry, II
(74) *Attorney, Agent, or Firm* — Vista IP Law Group LLP

(57) ABSTRACT

Catheter assembly including an elongate shaft comprising a thermoplastic polymer such as a thermoplastic shape memory polymer having a pre-selected glass transition temperature (Tg) and a means for heating the thermoplastic polymer, wherein the thermoplastic polymer is in a rubbery state at temperatures above the glass transition temperature and is in a glassy state at temperatures below the glass transition temperature. The elongate shaft may be selectively heated and cooled to provide sufficient flexibility and retention during a medical procedure.

20 Claims, 6 Drawing Sheets

U.S. PATENT DOCUMENTS

| | | |
|---|---|---|
| 4,627,436 A | 12/1986 | Leckrone |
| 4,636,346 A | 1/1987 | Gold et al. |
| 4,643,186 A | 2/1987 | Rosen et al. |
| 4,654,024 A | 3/1987 | Crittenden et al. |
| 4,655,771 A | 4/1987 | Wallsten |
| 4,672,962 A | 6/1987 | Hershenson |
| 4,685,458 A | 8/1987 | Leckrone |
| 4,690,175 A | 9/1987 | Ouchi et al. |
| 4,705,511 A | 11/1987 | Kocak |
| 4,728,322 A | 3/1988 | Walker et al. |
| 4,735,620 A | 4/1988 | Ruiz |
| 4,735,796 A | 4/1988 | Gordon |
| 4,740,674 A | 4/1988 | Tsutsumi |
| 4,747,405 A | 5/1988 | Leckrone |
| 4,748,979 A | 6/1988 | Hershenson |
| 4,753,223 A * | 6/1988 | Bremer .................. 600/140 |
| 4,767,611 A | 8/1988 | Gordon |
| 4,790,311 A | 12/1988 | Ruiz |
| 4,807,620 A | 2/1989 | Strul et al. |
| 4,817,613 A | 4/1989 | Jaraczewski et al. |
| 4,838,859 A | 6/1989 | Strassmann |
| 4,838,879 A | 6/1989 | Tanabe et al. |
| 4,840,622 A * | 6/1989 | Hardy .................. 604/264 |
| 4,842,590 A | 6/1989 | Tanabe et al. |
| 4,863,442 A | 9/1989 | DeMello et al. |
| 4,869,248 A | 9/1989 | Narula |
| 4,895,168 A | 1/1990 | Machek |
| 4,898,591 A | 2/1990 | Jang et al. |
| 4,899,787 A | 2/1990 | Ouchi et al. |
| 4,923,437 A | 5/1990 | Gordon |
| 4,930,494 A | 6/1990 | Takehana et al. |
| 4,950,258 A | 8/1990 | Kawai et al. |
| 4,981,478 A | 1/1991 | Evard et al. |
| 4,984,581 A | 1/1991 | Stice |
| 5,009,655 A | 4/1991 | Daignault, Jr. et al. |
| 5,017,259 A | 5/1991 | Kohsai |
| 5,019,040 A | 5/1991 | Itaoka et al. |
| 5,025,799 A | 6/1991 | Wilson |
| 5,041,089 A | 8/1991 | Mueller et al. |
| 5,047,025 A | 9/1991 | Taylor et al. |
| 5,055,101 A | 10/1991 | McCoy |
| 5,057,092 A | 10/1991 | Webster, Jr. |
| 5,069,674 A | 12/1991 | Fearnot et al. |
| 5,078,702 A | 1/1992 | Pomeranz |
| 5,087,256 A | 2/1992 | Taylor et al. |
| 5,090,956 A | 2/1992 | McCoy |
| 5,093,385 A | 3/1992 | Ali |
| 5,098,429 A | 3/1992 | Sterzer |
| 5,116,317 A | 5/1992 | Carson et al. |
| 5,143,085 A | 9/1992 | Wilson |
| 5,156,596 A | 10/1992 | Balbierz et al. |
| 5,160,559 A | 11/1992 | Scovil et al. |
| 5,163,431 A | 11/1992 | Griep |
| 5,176,660 A | 1/1993 | Truckai |
| 5,180,376 A | 1/1993 | Fischell |
| 5,190,520 A | 3/1993 | Fenton, Jr. et al. |
| 5,190,540 A | 3/1993 | Lee |
| 5,203,772 A | 4/1993 | Hammerslag et al. |
| 5,211,183 A | 5/1993 | Wilson |
| 5,217,440 A | 6/1993 | Frassica |
| 5,221,270 A | 6/1993 | Parker |
| 5,221,372 A | 6/1993 | Olson |
| 5,222,949 A | 6/1993 | Kaldany |
| 5,234,416 A | 8/1993 | Macaulay |
| 5,249,585 A | 10/1993 | Turner et al. |
| 5,254,107 A | 10/1993 | Soltesz |
| 5,257,635 A | 11/1993 | Langberg |
| 5,279,596 A | 1/1994 | Castaneda et al. |
| 5,290,230 A | 3/1994 | Ainsworth et al. |
| 5,298,532 A | 3/1994 | Ali |
| 5,306,252 A | 4/1994 | Yutori et al. |
| 5,308,342 A | 5/1994 | Sepetka et al. |
| 5,318,999 A | 6/1994 | Mitra et al. |
| 5,334,168 A | 8/1994 | Hemmer |
| 5,335,305 A | 8/1994 | Kosa et al. |
| 5,344,444 A | 9/1994 | Glastra |
| 5,349,946 A | 9/1994 | McComb |
| 5,358,493 A | 10/1994 | Schweich, Jr. et al. |
| 5,368,591 A | 11/1994 | Lennox et al. |
| 5,370,109 A * | 12/1994 | Cuny .................. 600/204 |
| 5,423,773 A | 6/1995 | Jimenez |
| 5,423,774 A | 6/1995 | Fischell et al. |
| 5,433,200 A | 7/1995 | Fleischhacker |
| 5,441,489 A * | 8/1995 | Utsumi et al. .................. 604/525 |
| 5,443,495 A | 8/1995 | Buscemi et al. |
| 5,445,624 A | 8/1995 | Jimenez |
| 5,449,369 A | 9/1995 | Imran |
| 5,449,703 A | 9/1995 | Mitra et al. |
| 5,464,419 A | 11/1995 | Glastra |
| 5,497,786 A | 3/1996 | Urick |
| 5,502,087 A | 3/1996 | Tateosian et al. |
| 5,509,910 A | 4/1996 | Lunn |
| 5,511,547 A | 4/1996 | Markle et al. |
| 5,514,108 A | 5/1996 | Stevens |
| 5,529,653 A | 6/1996 | Glastra |
| 5,531,685 A | 7/1996 | Hemmer et al. |
| 5,531,715 A | 7/1996 | Engelson et al. |
| 5,538,512 A | 7/1996 | Zenzon et al. |
| 5,545,151 A | 8/1996 | O'Connor et al. |
| 5,569,218 A | 10/1996 | Berg |
| 5,578,008 A | 11/1996 | Hara |
| 5,591,199 A | 1/1997 | Porter et al. |
| 5,599,319 A | 2/1997 | Stevens |
| 5,603,705 A | 2/1997 | Berg |
| 5,626,136 A | 5/1997 | Webster, Jr. |
| 5,658,263 A | 8/1997 | Dang et al. |
| 5,662,621 A | 9/1997 | Lafontaine |
| 5,662,622 A | 9/1997 | Gore et al. |
| 5,665,063 A | 9/1997 | Roth et al. |
| 5,674,208 A | 10/1997 | Berg et al. |
| 5,676,659 A | 10/1997 | McGurk |
| 5,711,909 A | 1/1998 | Gore et al. |
| 5,766,204 A | 6/1998 | Porter et al. |
| 5,769,796 A | 6/1998 | Palermo et al. |
| 5,772,628 A | 6/1998 | Bacich et al. |
| 5,779,673 A | 7/1998 | Roth et al. |
| 5,792,401 A | 8/1998 | Burnham |
| 5,800,500 A | 9/1998 | Spelman et al. |
| 5,810,867 A | 9/1998 | Zarbatany et al. |
| 5,810,874 A | 9/1998 | Lefebvre |
| 5,830,224 A | 11/1998 | Cohn et al. |
| 5,836,925 A | 11/1998 | Soltesz |
| 5,891,082 A | 4/1999 | Leone et al. |
| 5,891,094 A | 4/1999 | Masterson et al. |
| 5,897,537 A | 4/1999 | Berg et al. |
| 5,911,715 A | 6/1999 | Berg et al. |
| 5,911,737 A | 6/1999 | Lee et al. |
| 5,938,623 A | 8/1999 | Quiachon et al. |
| 5,951,495 A | 9/1999 | Berg et al. |
| 5,954,651 A | 9/1999 | Berg et al. |
| 5,957,966 A | 9/1999 | Schroeppel et al. |
| 5,971,979 A | 10/1999 | Joye et al. |
| 5,997,526 A * | 12/1999 | Giba et al. .................. 604/531 |
| 5,997,570 A | 12/1999 | Ligtenberg et al. |
| 6,006,756 A | 12/1999 | Shadduck |
| 6,017,323 A | 1/2000 | Chee |
| 6,017,335 A | 1/2000 | Burnham |
| 6,027,450 A | 2/2000 | Brown et al. |
| 6,030,405 A | 2/2000 | Zarbatany et al. |
| 6,042,578 A | 3/2000 | Dinh et al. |
| 6,056,844 A | 5/2000 | Guiles et al. |
| 6,059,815 A | 5/2000 | Lee et al. |
| 6,072,154 A | 6/2000 | Maynard |
| 6,076,609 A | 6/2000 | Job |
| 6,086,599 A | 7/2000 | Lee et al. |
| 6,090,099 A | 7/2000 | Samson et al. |
| 6,102,917 A | 8/2000 | Maitland et al. |
| 6,102,933 A | 8/2000 | Lee et al. |
| 6,123,718 A | 9/2000 | Tu et al. |
| 6,165,166 A | 12/2000 | Samuelson et al. |
| 6,169,269 B1 | 1/2001 | Maynard |
| 6,179,824 B1 | 1/2001 | Eggers et al. |
| 6,183,443 B1 | 2/2001 | Kratoska et al. |
| 6,193,705 B1 | 2/2001 | Mortier et al. |
| 6,197,844 B1 | 3/2001 | Hamrock et al. |
| 6,210,393 B1 | 4/2001 | Brisken |
| 6,212,422 B1 | 4/2001 | Berg et al. |

| | | |
|---|---|---|
| 6,224,610 B1 | 5/2001 | Ferrera |
| 6,240,231 B1 | 5/2001 | Ferrera et al. |
| 6,258,195 B1 | 7/2001 | Holman et al. |
| 6,272,371 B1 | 8/2001 | Shlomo |
| 6,287,320 B1 | 9/2001 | Slepian |
| 6,290,692 B1 | 9/2001 | Klima et al. |
| 6,296,622 B1 | 10/2001 | Kurz et al. |
| 6,323,251 B1 | 11/2001 | Perez et al. |
| 6,355,029 B1 | 3/2002 | Joye et al. |
| 6,387,052 B1 | 5/2002 | Quinn et al. |
| 6,388,043 B1 | 5/2002 | Langer et al. |
| 6,428,534 B1 | 8/2002 | Joye et al. |
| 6,428,563 B1 | 8/2002 | Keller |
| 6,468,297 B1 | 10/2002 | Williams et al. |
| 6,485,512 B1 | 11/2002 | Cheng |
| 6,520,952 B1 | 2/2003 | Jimenez |
| 6,533,752 B1 | 3/2003 | Waram et al. |
| 6,555,288 B1 | 4/2003 | Xu et al. |
| 6,562,021 B1 | 5/2003 | Derbin et al. |
| 6,579,913 B2 | 6/2003 | Klinkenberg et al. |
| 6,598,280 B1 | 7/2003 | Giba et al. |
| 6,720,402 B2 | 4/2004 | Langer et al. |
| 6,740,094 B2 | 5/2004 | Maitland et al. |
| 6,740,107 B2 * | 5/2004 | Loeb et al. .................. 607/89 |
| 7,018,346 B2 | 3/2006 | Griffin et al. |
| 7,351,199 B2 | 4/2008 | Nash |
| 2001/0026666 A1 * | 10/2001 | Ferrera et al. ................. 385/123 |
| 2001/0039412 A1 | 11/2001 | Fariabi |
| 2002/0026192 A1 | 2/2002 | Schmiel et al. |
| 2002/0095169 A1 | 7/2002 | Maitland et al. |
| 2002/0165520 A1 | 11/2002 | Forman |
| 2003/0069522 A1 | 4/2003 | Jacobsen et al. |
| 2003/0069539 A1 | 4/2003 | Gandhi et al. |
| 2003/0114914 A1 | 6/2003 | Cheng |
| 2003/0125710 A1 * | 7/2003 | Pepin ........................... 604/525 |
| 2003/0236533 A1 | 12/2003 | Wilson et al. |
| 2004/0054301 A1 | 3/2004 | Cassell |
| 2004/0104512 A1 | 6/2004 | Eidenschink |
| 2005/0149176 A1 | 7/2005 | Heggestuen et al. |
| 2006/0074401 A1 * | 4/2006 | Ross ........................... 604/525 |
| 2006/0127561 A1 | 6/2006 | Griffin et al. |

FOREIGN PATENT DOCUMENTS

| | | |
|---|---|---|
| EP | 0277366 | 8/1988 |
| EP | 0382974 | 8/1990 |
| EP | 0417865 | 3/1991 |
| EP | 0420993 | 4/1991 |
| EP | 0473045 | 3/1992 |
| EP | 0555088 | 8/1993 |
| JP | 4-40652 | 4/1992 |
| JP | 5-84303 | 4/1993 |
| JP | 10-156942 | 6/1998 |
| WO | WO 86/03980 | 7/1986 |
| WO | WO 92/15356 | 9/1992 |
| WO | WO 93/15785 | 8/1993 |
| WO | WO 95/10321 | 4/1995 |
| WO | WO 95/29722 | 11/1995 |
| WO | WO 96/20750 | 7/1996 |
| WO | WO 97/14466 | 4/1997 |
| WO | WO 00/03756 | 1/2000 |
| WO | WO 02/078777 | 10/2002 |

OTHER PUBLICATIONS

Gleich, Bernhard, "Catheter Temperature Measurement with Ferromagnets," *Research Disclosure*, Feb. 2001, p. 189.

Suwanwatana, W., Research Poster—University of Delaware "Inductions Heating of Thin Films Containing Ferromagnetic Particles", www.ccm.udel.edu/publications/AR/posters/PS/Suwanwatana, Mar. 18, 2002, 2 pages.

* cited by examiner

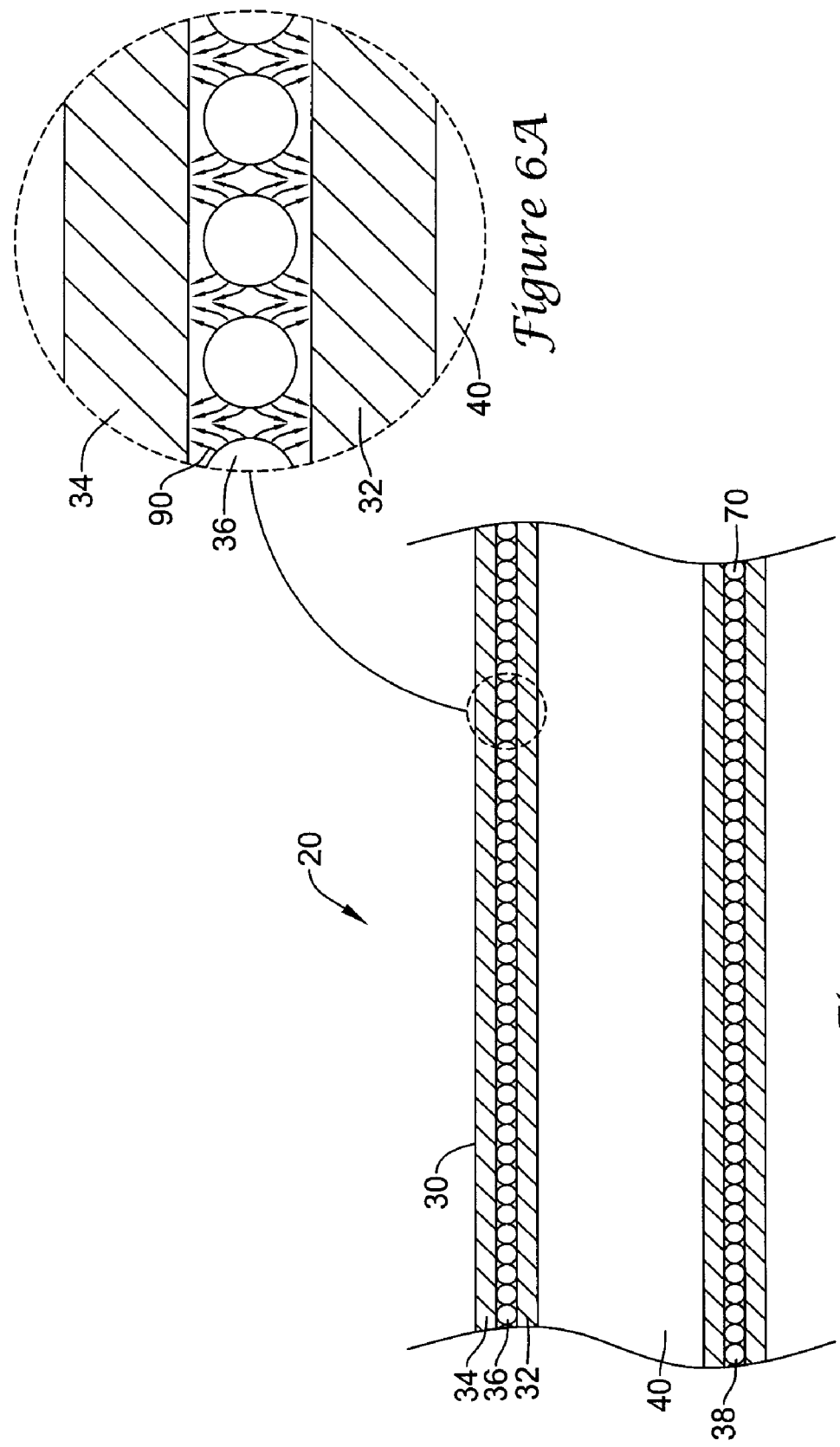

SELECTIVELY FLEXIBLE CATHETER AND METHOD OF USE

RELATED APPLICATIONS

This application is a continuation of co-pending U.S. application Ser. No. 11/004,544, filed Dec. 3, 2004, the entire disclosure of which is incorporated herein by reference.

FIELD OF THE INVENTION

The invention generally relates to catheters and more specifically to catheters having improved flexibility to navigate very tortuous vessels while maintaining sufficient stability at a distal site.

BACKGROUND OF THE INVENTION

Intravascular catheters are used in a wide variety of relatively non-invasive medical procedures. Such intravascular catheters may be used for diagnostic or therapeutic purposes. Generally, an intravascular catheter allows a physician to remotely perform a medical procedure by inserting the catheter into the vascular system of the patient at a location that is easily accessible and thereafter navigating the catheter to the desired target site. Vascular passageways distal of the insertion point, such as the neurovascular system, are often narrow and quite tortuous. Furthermore, in order to navigate through the patient's tortuous vascular system, intravascular catheters must be very flexible. If a catheter is sufficiently flexible to reach and pass through the tortuous vasculature, the catheter may lack sufficient column strength or stability to remain in position while, for example, subsequent treatment devices are advanced through the catheter.

It is desirable for an intravascular catheter having sufficient flexibility to reach tortuous vasculature be able to retain a sufficient amount of rigidity while positioned at the target site in order to provide stability and back-out support during a subsequent medical procedure.

SUMMARY OF THE INVENTION

The invention is directed to a catheter having sufficient flexibility to reach remote areas of the vasculature, yet providing rigidity while positioned at the target site to provide back-out support while additional treatment devices are advanced through the catheter. Such a catheter, for example, may provide sufficient flexibility to navigate to remote vessels, such as the neurovascular system, yet offer stability while delivering a therapeutic device, such as an embolic coil, to a target site.

Accordingly, one embodiment of the invention is a catheter including an elongate shaft comprising a shape memory material such as a shape memory polymer, having a pre-selected glass transition temperature (Tg). The shape memory polymer retains relatively stiff, glassy characteristics at temperatures below the glass transition temperature and becomes relatively flexible and rubbery at temperatures above the glass transition temperature.

In one embodiment of the invention, a means for heating the shape memory polymer is provided. Such means for heating may include light energy, electrical resistance heating, RF electromagnetic heating, ultrasonic heating, radiation energy, and fluid conduction heating, to name a few. For example, a guidewire may extend through the catheter lumen. The guidewire may be subjected to thermal energy by a heating means. For example, the guidewire may be connected to an electrical source, wherein thermal energy is created by electrical resistance along the guidewire. Alternatively, or additionally, a coil may be provided in the catheter, wherein the thermal energy is created by such means as electrical resistance along the coil.

The present invention further includes a method for placement and retention of a catheter within a vasculature. A catheter within the scope of the invention may be heated above a glass transition temperature (Tg) to become flexible and rubbery. While in a flexible state, the catheter may be positioned within the vasculature, conforming to the curvature of the vasculature. Once positioned in the vasculature, the catheter may then be cooled below a glass transition temperature (Tg) to become stiffer. While in the stiff, glassy state, the catheter retains the curvature formed in the catheter following the curvature of the vasculature pathway. By retaining this curvature, the catheter provides enhanced retention and back-out support during a medical procedure.

BRIEF DESCRIPTION OF THE DRAWINGS

The invention may be more completely understood in consideration of the following detailed description of various embodiments of the invention in connection with the accompanying drawings, in which:

FIG. 6 is a cross-sectional view of a portion of a catheter assembly selectively heating a portion of a catheter in accordance with the invention; and FIG. 6A is an enlarged view of FIG. 6 showing thermal energy generated from a coil for selectively heating a portion of a catheter in accordance with the invention.

DETAILED DESCRIPTION OF PREFERRED EMBODIMENTS

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention.

Figure 1:
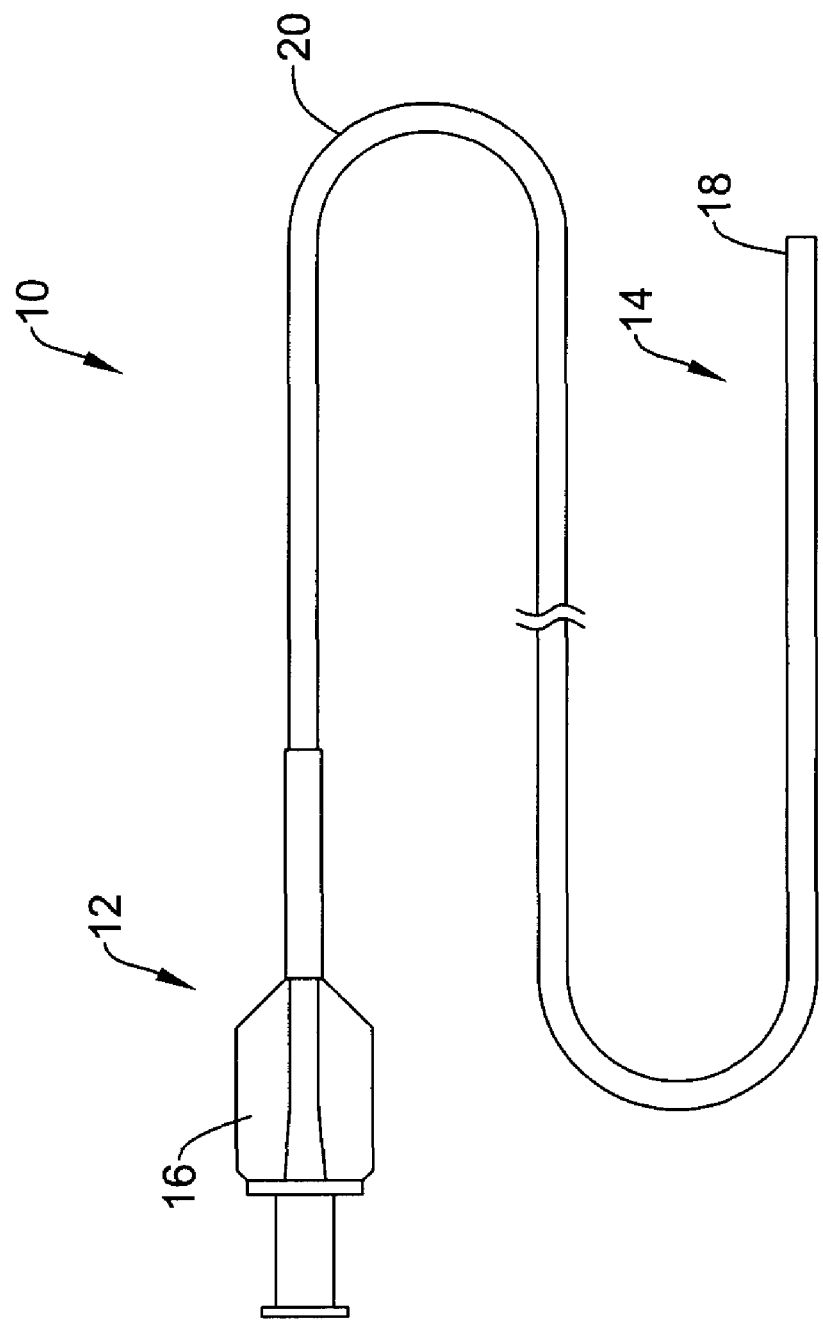
FIG. 1 is a plan view of a catheter according to the invention.

As shown in FIG. 1, the invention generally relates to a catheter 10 including an elongate shaft 20 extending from a proximal end 12 to a distal end 14. The catheter 10 may include a hub 16 near the proximal end 12 and a distal tip 18 near the distal end 14.

Figure 2:
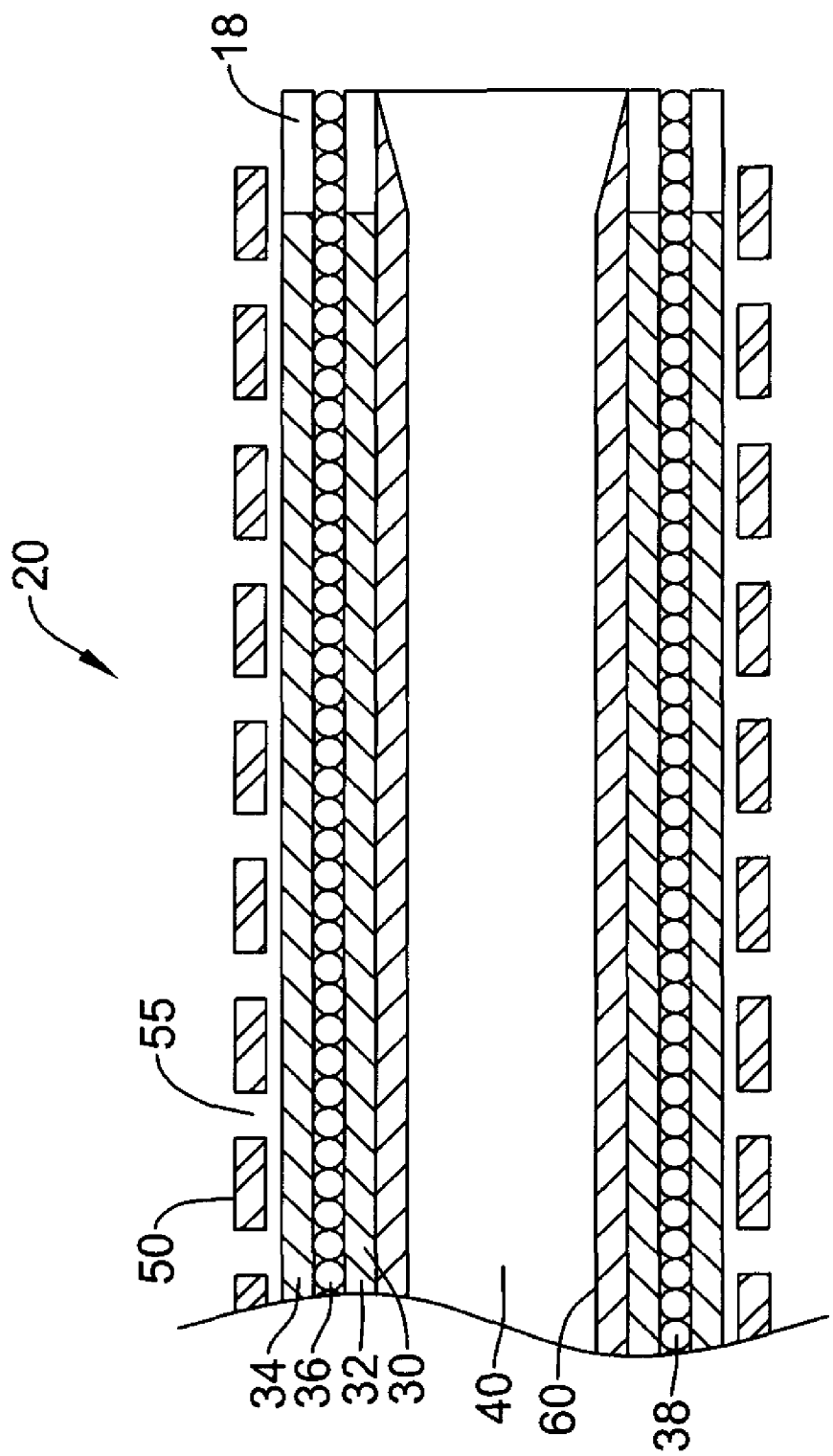
FIG. 2 is a cross-sectional view of a portion of a catheter in accordance with the invention.

FIG. 2 is a cross-sectional view of a portion of the catheter 10 according to one embodiment of the invention. The portion of the catheter 10 shown in FIG. 2 is a distal portion of the catheter 10 including the distal tip 18; however, similar features depicted in FIG. 2 may be located at more proximal locations of the elongate shaft 20 instead of, or in addition to, those located along a distal portion of the catheter 10.

The elongate shaft 20 may include a polymer layer 30. The polymer layer 30 may be formed of a material such as high-density polyethylene (HDPE), low-density polyethylene (LDPE), silicone, fluoropolymer, liquid crystal polymer (LCP), polyimide, polyamide, polyester, polyethylene (PE), polypropylene, polyvinyl chloride (PVC), polyfluorocarbon, polyurethane, polysulfone, ethyl vinyl acetate (EVA), polyether block amide (PEBAX), styrene-ethylene/butylenes-styrene (SEBS), styrene-butadiene-styrene (SBS), polyethylene terephthalate (PET), and their mixtures, alloys, blends, copolymers, and block copolymers. Preferably, polymer layer 30 may comprise a thermoplastic polymer having a glass transition temperature. A thermoplastic polymer, in contrast with a thermoset polymer, may have the capabilities of being repeatedly softened by heating and hardened by cooling within a temperature range corresponding to a temperature such as a glass transition temperature. Therefore, a thermoplastic polymer may be repeatedly heated and reshaped. On the other hand, a thermoset polymer, once initially formed by crosslinking, irreversibly retains that pre-shaped form and may not be softened by heating to take on a new form.

More preferably, polymer layer 30 may comprise a thermoplastic shape memory polymer, such as a polyurethane-based polymer, having a pre-selected glass transition temperature. The shape memory polymer retains relatively stiff, glassy characteristics at temperatures below the glass transition temperature and becomes relatively flexible and rubbery at temperatures above the glass transition temperature. Preferably, the glass transition temperature is selected to be greater than the body temperature of the patient during treatment. The glass transition temperature may be greater than about 37° C., for example. The glass transition temperature may be selected in the range of about 38° C. to about 80° C., or more preferably in the range of about 50° C. to about 80° C. Most preferably, the glass transition temperature may be selected in the range of about 60° C. to about 70° C. Shape memory polymers are preferred to other polymers due to their relatively sharp transition from a glassy state to a rubbery state. Additionally, the hardness variation between the glassy state and the rubbery state may be in the range of 200%. For example, a thermoplastic shape memory polymer within the scope of the invention may have a durometer hardness of 75-80 D in the glassy state and a durometer hardness of 25-30 D in the rubbery state. Additionally, shape memory polymers may possess greater integrity than other potential polymers when subjected to multiple iterations across the glass transition temperature.

A thermoplastic shape memory polymer may be characterized as a polymer that undergoes a phase transformation at a manufactured temperature, such as the glass transition temperature of the polymer. After the material is polymerized, the polymer is molded into its memory shape. The polymer is rubbery at temperatures above the glass transition temperature, whereby the polymer is flexible and may easily be flexed into an arbitrary form. The polymer retains this arbitrary form when the temperature falls below the glass transition temperature. Below the glass transition temperature, the polymer becomes relatively stiff in the glassy state. If the polymer is reheated above the glass transition temperature, the polymer will return to its original memory shape if unrestrained.

The polymer layer 30 may extend substantially the entire length of the elongate shaft 20 or a portion thereof. The polymer layer 30 may extend along a distal portion of the elongate shaft 20 to provide a region having improved flexibility and retention capabilities. As shown in FIG. 2, polymer layer 30 may include an inner layer 32 and an outer layer 34. However, polymer layer 30 may comprise a single layer.

Figure 3:
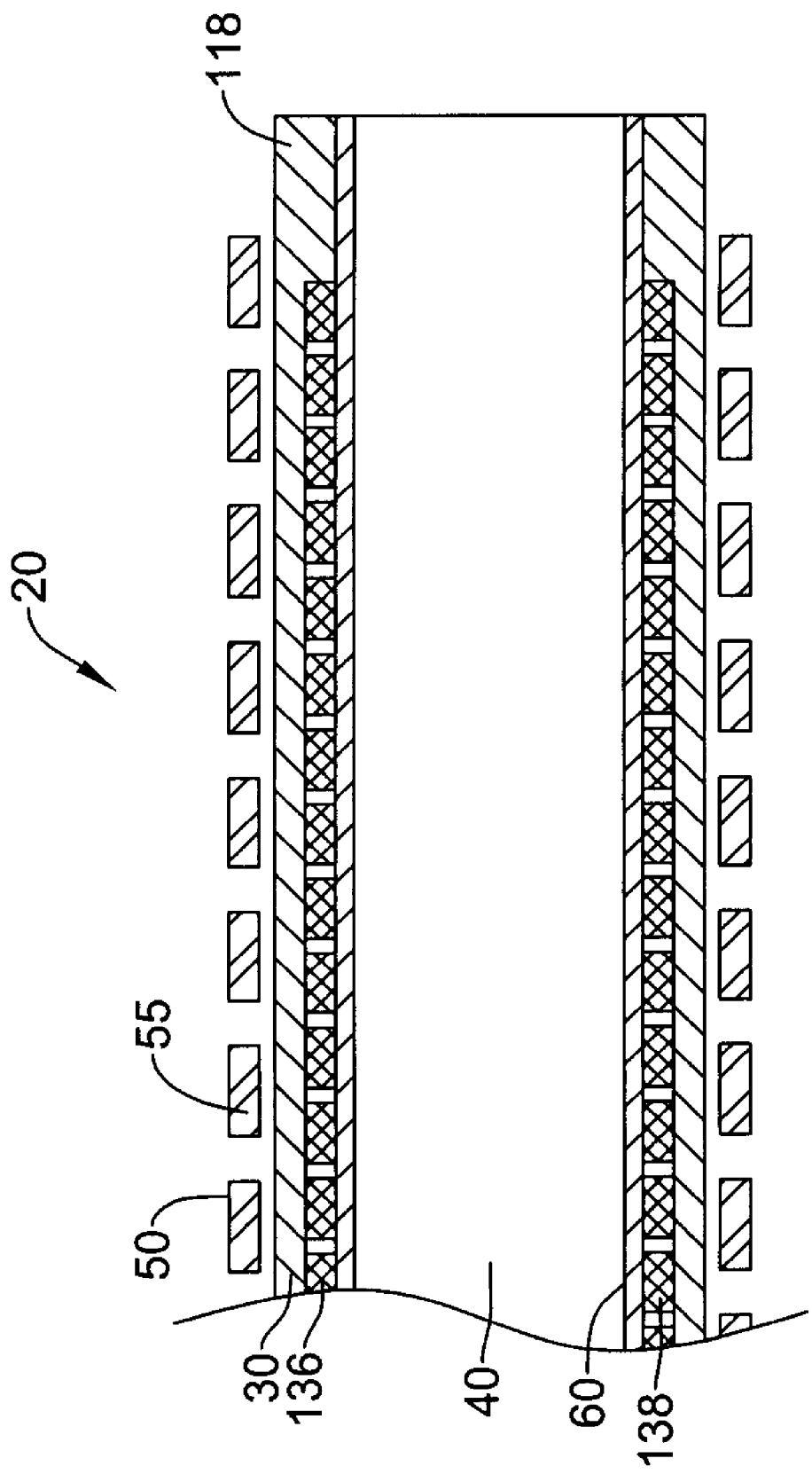
FIG. 3 is a cross-sectional view of a portion of a catheter in accordance with the invention.

A reinforcement member 36 may be disposed along at least a portion of the polymer layer 30. Reinforcement member 36 may be disposed along an inner surface of the polymer layer 30 or along an outer surface of the polymer layer 30. As shown in FIG. 2, reinforcement member 36 may be disposed between at least a portion of the inner layer 32 and the outer layer 34 of polymer layer 30. Alternatively, reinforcement member 36 may be disposed within at least a portion of polymer layer 30. Reinforcement member 36 may be a heat conductive reinforcement member. Reinforcement member 36 may be a coil helically wound along at least a portion of the length of elongate shaft 20. Alternatively, reinforcement member 36 may be a braid woven along at least a portion of the length of the elongate shaft 20. Reinforcement member 36 may comprise one or more filaments 38. Filaments 38 may have a circular cross-sectional profile or filaments 38 may have a relatively flat cross-sectional profile such as is shown in FIG. 3. It is contemplated that filaments 38 may have any perceivable cross-sectional profile.

Elongate shaft 10 may include an outer tubular member 50 disposed about at least a portion of polymer member 30. Some examples of some suitable materials may include stainless steels (e.g., 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

Outer tubular member 50 may include a plurality of apertures 55 formed along the length of outer tubular member 50 to increase the flexibility of the elongate shaft 20 to a desired level. Apertures 55 may be slots, slits, grooves, helical cuts, or the like. The spacing, depth and type of apertures 55 may be varied to control the flexure profile and torsional stiffness of the outer tubular member 50. The spacing of apertures 55 may vary gradually along outer tubular member 50, or may change incrementally. Apertures 55 may extend through the wall of the outer tubular member 50, or they may extend only partially through the wall. It is contemplated that at least some of the apertures extend through the wall of the outer tubular member 50. Apertures 55 may be micromachined into the outer tubular member 50 by electrostatic discharge machining (EDM), chemical milling, ablation, laser cutting, saw cutting, grinding, etching, or the like. Apertures 55 may extend substantially the full length of the elongate shaft 20, or apertures may be positioned along selected portions of the elongate shaft 20 where increased flexibility is desired. Such techniques for creating apertures 55 along the outer tubular member 50 are discussed in detail in U.S. Patent Publication 2003/0069522 to Jacobsen et al., as herein incorporated by reference in its entirety.

The elongate shaft 20 may include an inner liner 60. Preferably, inner liner 60 comprises polytetrafluoroethylene (PTFE). Polytetrafluoroethylene is a preferred material because it creates a smooth, low friction surface for the passage of other devices or fluids through the lumen 40 of elongate shaft 20. In an alternate embodiment, inner liner 60 may comprise materials including, but not limited to, thermoplastics, high performance engineering resins, fluorinated ethylene propylene (FEP), polymer, polyethylene (PE), polypropylene (PP), polyvinylchloride (PVC), polyurethane, polyether-ether ketone (PEEK), polyimide, polyamide, polyphenylene sulfide (PPS), polyphenylene oxide (PPO) polysulfone, nylon, or perfluoro(propyl vinyl ether (PFA).

A distal tip 18 may be disposed at the distal end 14 of elongate shaft 20. Distal tip 18 may comprise any of a number of suitable polymers or polymer blends. For example, distal tip 18 may comprise a polyether block amide (PEBAX®). Preferably distal tip has a low durometer hardness in the range of about 40 A about 60 D. As shown in FIG. 2, reinforcement member 36 extends into at least a portion of distal tip 18. However, distal tip 18 may extend distal of the reinforcement member 36 or abut reinforcement member 36 at the distal end 14 of the elongate shaft 20. Preferably, distal tip 18 may extend approximately 5 cm. or less.

An alternate embodiment is shown in FIG. 3. Elongate shaft 20 may include a reinforcement member 136 including at least one filament 138 having a flat ribbon profile. Reinforcement member 136 may be a helical coil or a braid member. A polymer layer 30 may be disposed adjacent the reinforcement member 136 and may extend substantially the entire length of the elongate shaft, or any portion thereof. As shown in FIG. 3, the polymer layer 30 may be disposed about the reinforcement member 136. An inner liner 60, as discussed above, may be disposed in the lumen 40 of the elongate shaft 20. Outer tubular member 50 having a plurality of apertures 55 may be disposed about at least a portion of the polymer layer 30. Preferably, outer tubular member extends substantially the entire length of the elongate shaft 20. As shown in FIG. 3, polymer layer 30 may extend distal of the reinforcement member 136 and/or the outer tubular member 50 to define a distal tip 118.

Figure 4:
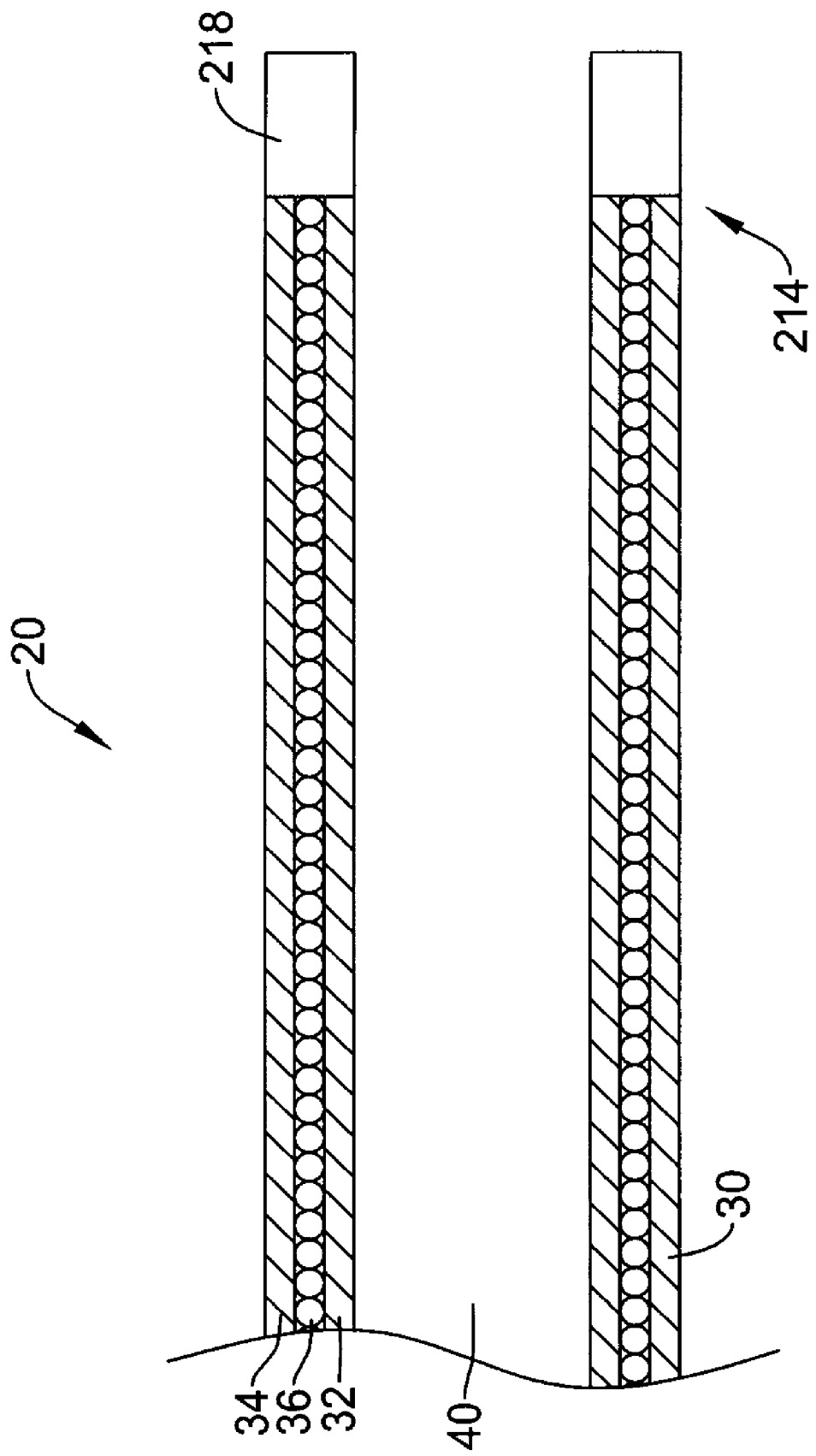
FIG. 4 is a cross-sectional view of a portion of a catheter in accordance with the invention.

Another embodiment of the invention is shown in FIG. 4. Elongate shaft 20 may include a reinforcement member 36 disposed between an outer layer 34 and an inner layer 32 of polymer layer 30. The reinforcement member 36 and polymer layer 30 may extend to the distal end 214 of the elongate shaft 20. A distal tip 218 may abut the distal end 214 of the elongate shaft 20 and extend distally to provide a soft atraumatic tip. As shown in FIG. 4, elongate shaft 20 or a portion thereof need not include an outer tubular member 34.

Figure 5:
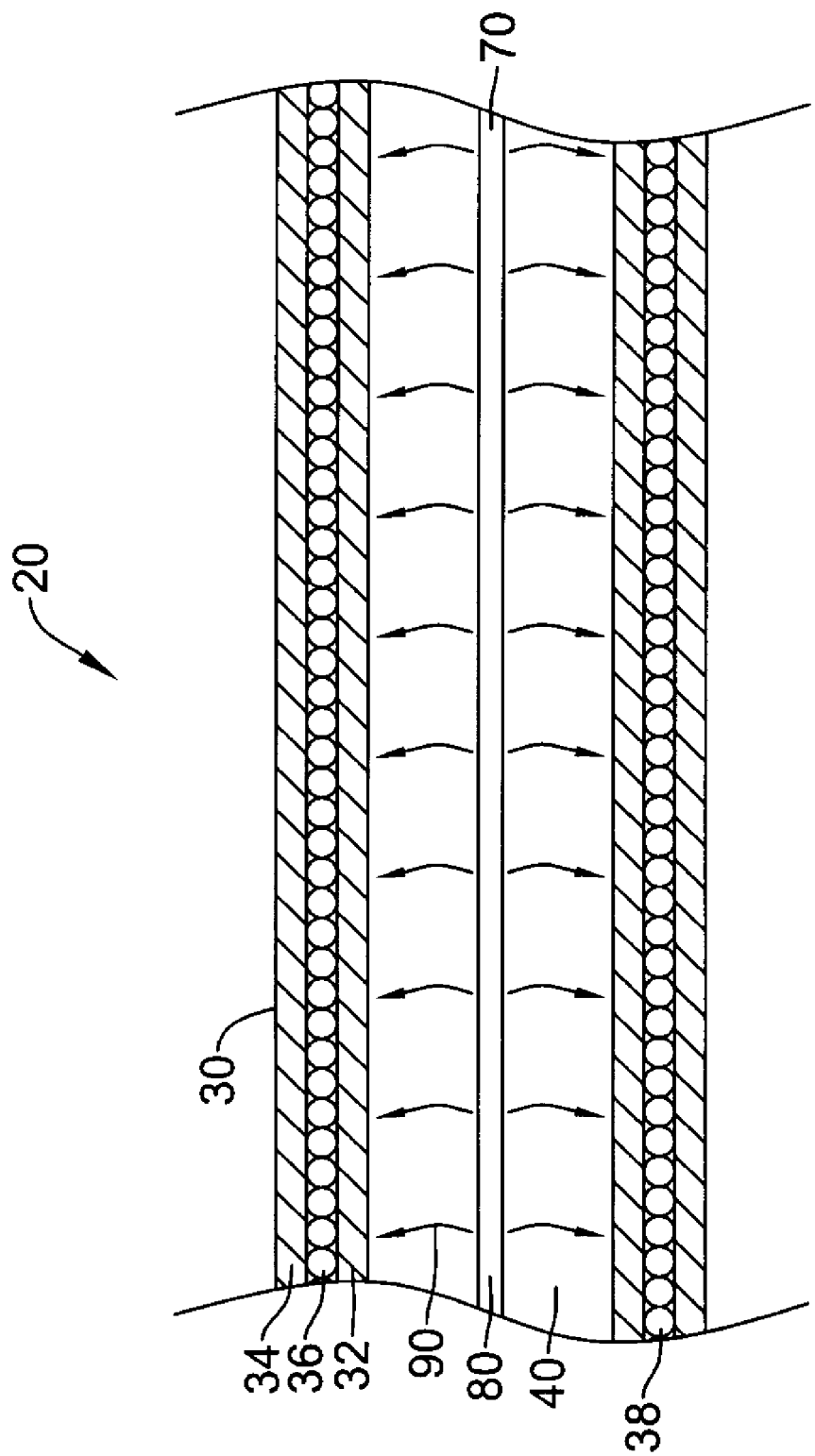
FIG. 5 is a cross-sectional view of a portion of a catheter assembly selectively heating a portion of a catheter in accordance with the invention.

In one embodiment of the invention, a means for heating the shape memory polymer is provided. Such means for heating may include light energy, electrical resistance heating, RF electromagnetic heating, ultrasonic heating, radiation heating, or fluid conduction heating, to name a few. For example, a heat conductive member 70 may be positioned along at least a portion of the polymer layer 30. Heat conductive member 70 may be a conductive wire connected to an electrical supply (not shown), wherein resistance in heat conductive member 70 creates thermal energy 90. Heat conductive member 70 may comprise at least one filament 38 of reinforcement member 36 or a guidewire 80, for example. As shown in FIG. 5, a guidewire 80 may extend through the lumen 40 of elongate shaft 20. The guidewire 80 may be connected to an electrical source (not shown), wherein thermal energy 90 is transferred, for example by electrical resistance, along the guidewire 80. Alternatively, or additionally, as shown in FIG. 6, at least one filament 38 of reinforcement member 36 may be provided along the elongate shaft 20, wherein thermal energy 90 is created by electrical resistance along the reinforcement member 36. As can be better shown in FIG. 6A, reinforcement member 36 may transmit thermal energy 90 to at least a portion of the polymer layer 30. It is contemplated that heat conductive member 70 may transfer thermal energy 90 to the polymer layer 30 by alternate means such as through RF heating, ultrasonic heating, laser heating, or the like.

A method of changing the flexibility of a catheter as described above for placement and retention in a vasculature will now be described. Prior to insertion in a patient's vasculature, elongate shaft 20 may be in its more rigid, glassy state, wherein polymer layer 30 is at a temperature below the glass transition temperature. Polymer layer 30 may be subjected to a thermal energy source, wherein thermal energy increases the temperature of the polymer layer above the glass transition temperature. The thermal energy source may be RF heating, electrical resistance heating, a chemical reaction, ultrasonic waves, radiation heating, fluid conduction heating, or light energy, to name a few. Above the glass transition temperature, the elongate shaft 20 may have increased flexibility for navigating a tortuous vasculature. While in the more flexible, rubbery state above the glass transition temperature, the elongate shaft 20 may be easily navigated through the vasculature, wherein the elongate shaft 20 takes on an arbitrary curvature complementing the vasculature pathway taken by the catheter 10 to a target site within the patient's body. Therefore, elongate shaft 20 need not have a pre-shaped curvature in order to navigate a tortuous vasculature and conform to a selected pathway. Once positioned at a target site in the vasculature, the polymer layer 30 of elongate shaft 20 is cooled below the glass transition temperature, wherein the polymer layer 30 transitions to a rigid, glassy state. The polymer layer 30 may be cooled naturally by the body as the temperature of the polymer layer equalizes with the body temperature, or the polymer layer 30 may be artificially cooled by other means such as by flushing the catheter 10 with a cooler fluid such as saline. As the polymer layer 30 is cooled below the glass transition temperature, the elongate shaft 20 retains its arbitrary curvature within the vasculature. Below the glass transition temperature, the elongate shaft 20 may be form cast to the curvature of the pathway through the vasculature. In this rigid configuration, the elongate shaft 20 exhibits increased stability and back-out support for the catheter 10. During a subsequent medical procedure, an additional medical device or devices may be delivered through the elongate shaft 20 to the target site. For example, embolic coils may be passed through the catheter 10 to a target site within the vasculature. The rigid state of the curvature retains the elongate shaft 20 at the target site during such a medical procedure and prevents the elongate shaft 20 from shifting in the vasculature. Since the elongate shaft 20 is in the rigid, glassy state while positioned in the vasculature, it is advantageous for the polymer layer 30 to have a glass transition temperature greater than the body temperature of the patient. In other words, for use in a human being, the glass transition temperature is preferably greater than about 37° C.

At the conclusion of a medical procedure, the elongate shaft 20 may be reheated above the glass transition temperature of the polymer layer 30. Once in its flexible, rubbery state, the elongate shaft may easily be withdrawn from the vasculature or repositioned at a subsequent target site within the body. Subsequent cycles of heating and cooling the elongate shaft may be performed as necessary during a medical procedure to provide selective flexibility and stability to the catheter.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What we claim is:

1. A method for treating tissue at a target location in a patient's body using a catheter, the catheter comprising a thermoplastic shape memory polymer having a glass transition temperature, the method comprising in the following order the steps of:
   (a) heating at least a distal portion of the catheter to raise a temperature of the polymer in the distal portion above the glass transition temperature to thereby render the distal portion of the catheter into a flexible state; and
   (b) positioning the distal portion of the catheter at the target location in the patient's body, wherein, after the distal portion is positioned at the target location, the polymer in the distal portion cools to a temperature lower than the glass transition temperature to thereby render the distal portion into a rigid state.

2. The method of claim 1, wherein, when the distal portion of the catheter is in its flexible state and positioned at the target location, the distal portion of the catheter assumes a shape complementary of a shape of the target location.

3. The method of claim 2, wherein, after the polymer in the distal portion of the catheter cools to a temperature lower than the glass transition temperature, the distal portion of the catheter retains the shape complementary of the shape of the target location.

4. The method of claim 1, further comprising the step of (c) administering a treatment through the catheter to tissue at the target location.

5. The method of claim 4, further comprising the steps of (d) heating at least the distal portion of the catheter while it is at the target location to thereby raise the temperature of the polymer in the distal portion above the glass transition temperature and render the distal portion of the catheter into its flexible state, and (e) withdrawing the catheter from the target location with the distal portion of the catheter in its flexible state.

6. The method of claim 1, wherein step (a) comprises heating a thermally conductive member disposed in or adjacent to the distal portion of the catheter.

7. The method of claim 6, wherein the thermally conductive member is selected from the group comprising a heat conductive coil, a heating guidewire, a light energy heating member, an electrical resistance heating member, an RF electromagnetic heating member, an ultrasonic heating member, a radiation heating member, and a fluid conduction heating member.

8. The method of claim 1, wherein step (b) comprises actively cooling the polymer in the distal portion of the catheter below the glass transition temperature.

9. The method of claim 8, wherein actively cooling the polymer in the distal portion comprises flushing the catheter with a liquid.

10. The method of claim 1, wherein the glass transition temperature is greater than a body temperature of the patient.

11. The method of claim 1, wherein the glass transition temperature is greater than about 37° C.

12. The method of claim 1, wherein the glass transition temperature is between about 38° C. and about 80° C.

13. The method of claim 1, wherein the glass transition temperature is between about 50° C. and about 80° C.

14. The method of claim 1, wherein the glass transition temperature is between about 60° C. and about 70° C.

15. The method of claim 1, wherein the target location is a vascular location.

16. A method for positioning a distal portion of a catheter at a target location in a patient's body, the catheter comprising a thermoplastic shape memory polymer having a glass transition temperature, the method comprising in the following order:
   passing current through an electrical resistance heating member disposed in or adjacent to the distal portion of the catheter to thereby raise a temperature of the polymer above the glass transition temperature and render the distal portion into a flexible state; and
   positioning the distal portion at the target location in the patient's body, wherein, after the distal portion is positioned at the target location, the polymer in the distal portion cools to a temperature lower than the glass transition temperature to thereby render the distal portion into a rigid state.

17. The method of claim 16, wherein the catheter comprises an inner layer and an outer layer, and the electrical resistance heating member is disposed between the inner and outer layers.

18. The method of claim 16, wherein, when the distal portion of the catheter is in its flexible state and positioned at the target location, the distal portion of the catheter assumes a shape complementary of a shape of the target location.

19. The method of claim 18, wherein, after the polymer in the distal portion of the catheter cools to a temperature lower than the glass transition temperature, the distal portion of the catheter retains the shape complementary of the shape of the target location.

20. The method of claim 17, wherein the inner and outer layers each comprise the thermoplastic shape memory polymer.

* * * * *